United States Patent [19]

Seo et al.

[11] Patent Number: 4,738,976
[45] Date of Patent: Apr. 19, 1988

[54] ANTIMYCOTIC AGENT AND FUNGICIDAL AGENT

[75] Inventors: Akira Seo, Yamatotakada; Hideo Kanno, Ibaraki; Nobu Hasegawa, Nishinomiya; Yukio Miyagi, Osaka; Akira Nishimura, Kawachinagano; Shigeo Konaka, Habikino; Tetsuto Ohmi, Kawachinagano; Yukimi Munechika, Hashimoto; Matazaemon Uchida, Kawachinagano; Kenichi Ikeda, Chiba, all of Japan

[73] Assignee: Nihon Nohyaku Co., Ltd., Tokyo, Japan

[21] Appl. No.: 916,653

[22] Filed: Oct. 8, 1986

Related U.S. Application Data

[62] Division of Ser. No. 786,123, Oct. 10, 1985.

[51] Int. Cl.$^4$ ............... A01N 43/40; A01N 43/50
[52] U.S. Cl. ................................ 514/341; 514/397
[58] Field of Search ............................ 514/341, 397

[56]  References Cited

U.S. PATENT DOCUMENTS 4,359,475  11/1982  Walker ........................... 514/397

Primary Examiner—Henry R. Jiles
Assistant Examiner—Robert C. Whittenbaugh
Attorney, Agent, or Firm—Cushman, Darby & Cushman

[57] ABSTRACT

A novel ketene S,S-acetal derivative which is useful as an antimycotic agent and an agricultural chemical of fungicidal, plant growth regulating or insecticidal properties represented by the general formula (I):

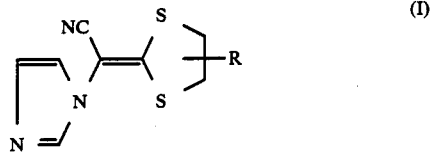

wherein R represents a hydrogen atom; an alkyl group having 1 to 8 carbon atoms; a cycloalkyl group having 3 to 6 carbon atoms; a methylene group; a lower alkenyl group; a lower alkyl group substituted by a halogen atom, a cyano group, a lower alkoxyl group, a lower alkylthio group; a carbamoyl group, an acyl group, or an alkenoyloxy group; a phenyl group represented by

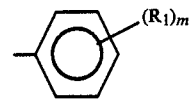

(in which $R_1$ represents a hydrogen atom, a halogen atom, a straight or branched chain lower alkyl group, a lower alkoxyl group which may be substituted by one or more halogen atoms, a phenoxy group or a methylenedioxy group, and m represents an integer of 1 to 3); a benzyl group; a methylenedioxybenzyl group; a phenoxyalkyl group; a phenoxyalkyl group substituted by a halogen atom; a naphthyl group; or a substituted or unsubstituted pyridyl group.

16 Claims, No Drawings

ANTIMYCOTIC AGENT AND FUNGICIDAL AGENT

This is a division of application Ser. No. 786,123 filed Oct. 10, 1985.

BACKGROUND OF THE INVENTION

This invention relates to a novel ketene S,S-acetal derivatives which are useful as antimycotic agents and agricultural chemicals.

More particularly, this invention relates to ketene S,S-acetal derivatives represented by the general formula (I):

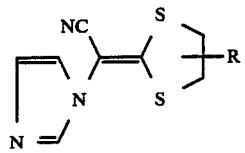

wherein R represents a hydrogen atom; an alkyl group having 1 to 8 carbon atom; a cycloalkyl group having 3 to 6 carbon atoms; a methylene group; a lower alkenyl group; a lower alkyl group substituted by a halogen atom, a cyano group, a lower alkoxy group, a lower alkylthio group, a carbamoyl group, an acyl group, or an alkenoyloxy group; a phenyl group represented by

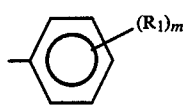

(in which $R_1$ represents a hydrogen atom, a halogen atom, a straight or branched chain lower alkyl group, a lower alkoxyl group which may be substituted by one or more halogen atoms, a phenoxy group or a methylenedioxy group, and m represents an integer of 1 to 3); a benzyl group; a methylenedioxybenzyl group; a phenoxyalkyl group; a phenoxyalkyl group substituted by a halogen atom; a naphthyl group; or a substituted or unsubstituted pyridyl group.

SUMMARY OF INVENTION

The present inventors have devoted themselves to research in order to invent a novel ketene S,S-acetal derivative, and have consequently found that compounds represented by the general formula (I) are novel compounds not described in literatures and are useful as antimycotic agents and agricultural chemicals; in particular, not only fungicides and plant growth regulators but also insecticides, whereby this invention has been accomplished.

The substituent R in the above general formula (I) includes hydrogen atom; straight or branched chain alkyl groups such as methyl, ethyl, n-propyl, i-propyl, n-butyl, i-butyl, s-butyl, t-butyl, n-pentyl, i-pentyl, neopentyl, n-hexyl, n-octyl and the like; cycloalkyl groups such as cyclopropyl, cyclohexyl and the like; methylene group; lower alkenyl groups such as vinyl, allyl and the like; lower alkyl groups substituted by a halogen atom such as chloromethyl, dichloroethyl and the like; lower alkyl groups substituted by a cyano group such as cyanomethyl and the like; lower alkyl groups substituted by a lower alkoxyl such as methoxymethyl, methoxyethyl and the like or a lower alkylthio group such as methylthiomethyl and the like; lower alkyl group substituted by carbamoyl group such as carbamoylmethyl and the like; lower alkyl groups substituted by an acyl group; lower alkyl groups substituted by an alkenoyloxy groups such as acryloylmethyl and the like; phenyl groups represented by

(in which $R_1$ represents a hydrogen atom, a halogen atom, a straight or branched chain lower alkyl group, a lower alkoxyl group which may be substituted by one or more halogen atoms, a phenoxy group or a methylenedioxy group, and m represents an integer of 1 to 3); a benzyl group; a methylenedioxybenzyl group; a phenoxyalkyl group such as phenoxymethyl and the like; a phenoxyalkyl group substituted by a halogen atom; naphthyl group; substituted or unsubstituted pyridyl group; etc.

DETAILED DESCRIPTION OF INVENTION

The compound represented by the general formula (I) of this invention can be synthesized, for example, by the process shown below:

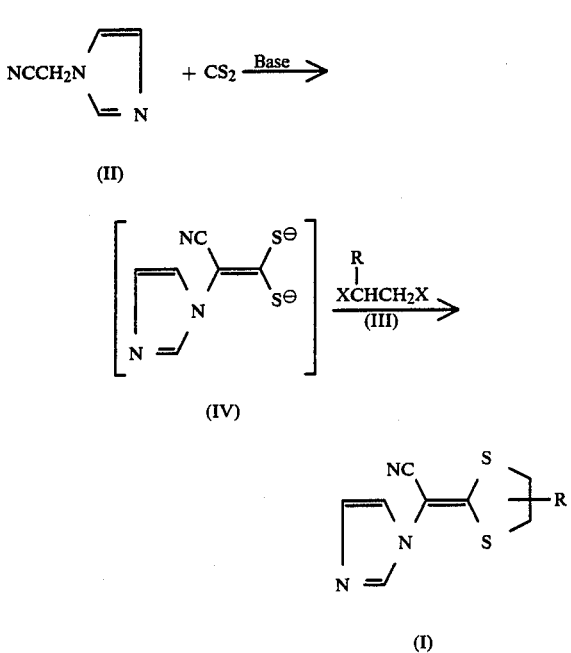

wherein R is as defined above, and X represents a halogen atom, a mesyloxy or a tosyloxy group. That is to say, the compound represented by the general formula (I) can be obtained by reacting 1-cyanomethylimidazole represented by the structural formula (II) with carbon disulfide in the presence of a base and a solvent to form an intermediate represented by the structural formula (IV), and reacting the intermediate with a compound represented by the general formula (III) without isolating the same.

As the solvent usable in the invention, any solvent may be used so long as it does not inhibit the progress of the reaction, and there can be exemplified, for example, alcohols such as methanol, ethanol, isopropanol and the like, dimethylsulfoxide, dimethylformamide, hexamethylenephosphoroamide, water, etc. These solvents can be used alone or as a mixture thereof.

As the base usable in this invention, there can be exemplified sodium carbonate, potassium carbonate, sodium hydrogencarbonate, potassium hydrogencarbonate, sodium hydroxide, potassium hydroxide, potassium t-butoxide, etc. These can be used in solid state or in solution.

Althougn it is sufficient that the reaction temperature is selected in the range of 0° to 100° C., it is particularly preferable to carry out the reaction at a temperature near room temperature.

It is sufficient that the reaction time is properly selected in the range of 0.5 to 24 hours.

It is sufficient that the amount of the base used is selected in the range of 2 to 4 moles per mole of 1-cyanomethylimidazole represented by the structural formula (IV).

It is sufficient that after completion of the reaction, the reaction solution is treated in the usual way. For example, the reaction product is extracted and separated with a suitable solvent and then can be purified by recrystallization or column chromatography.

The compound represented by the general formula (I) is often obtained as a mixture of two kinds of the geometrical isomers shown below.

(Z isomer)

(E isomer)

The aforesaid mixture of the Z and E isomers can often be isolated into the two isomers by a suitable separation method, for example, recrystallization, chromatography or the like.

This invention includes the geometrical isomers, i.e., the E and Z isomers, and all mixtures of the two isomers in any ratio.

Typical examples of the compounds represented by the general formula (I) are shown in Table 1, but this invention is not limited thereto.

TABLE 1

(I)

| Compound No. | R | Physical property, melting point, refractive index, NMR value (TMS/CDCl$_3$) |
|---|---|---|
| 1 | H | Melting point 126.5° C. |
| 2 | CH$_3$ | Melting point 97.6° C. |
| 3 | C$_2$H$_5$ | n$_D^{17}$ 1.6246 |
| 4 | n-C$_3$H$_7$ | n$_D^{27}$ 1.6065 |
| 5 | i-C$_3$H$_7$ | Melting point 86.7° C. (Z isomer) |
| 6 | i-C$_3$H$_7$ | Melting point 55.8° C. (E isomer) |
| 7 | n-C$_4$H$_9$ | n$_D^{27}$ 1.5830 |
| 8 | i-C$_4$H$_9$ | Melting point 73.3° C. (Z isomer) |
| 9 | i-C$_4$H$_9$ | Melting point 118.1° C. (F isomer) |
| 10 | s-C$_4$H$_9$ | n$_D^{16}$ 1.6011 (Z isomer) |
| 11 | s-C$_4$H$_9$ | n$_D^{16}$ 1.6089 (E isomer) |
| 12 | t-C$_4$H$_9$ | Melting point 151.7° C. |
| 13 | n-C$_5$H$_{11}$ | n$_D^{16.5}$ 1.5931 (Z isomer) |
| 14 | n-C$_5$H$_{11}$ | n$_D^{16.5}$ 1.5949 (E isomer) |
| 15 | i-C$_5$H$_{11}$ | Melting point 74.3° C. (Z isomer) |
| 16 | i-C$_5$H$_{11}$ | Melting point 111.4° C. (E isomer) |
| 17 | neo-C$_5$H$_{11}$ | Melting point 96.2° C. (Z isomer) |
| 18 | neo-C$_5$H$_{11}$ | Melting point 107.7° C. (E isomer) |
| 19 | n-C$_6$H$_{13}$ | n$_D^{17}$ 1.5908 (Z isomer) |
| 20 | n-C$_6$H$_{13}$ | Melting point 48.2° C. (E isomer) |
| 21 | 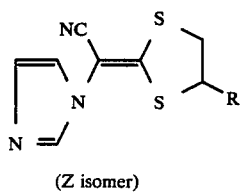 | Melting point 113.9° C. (Z isomer) |
| 22 | 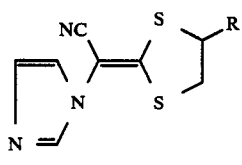 | Melting point 103.8° C. (E isomer) |
| 23 | =CH$_2$ | Melting point 115.7° C. |
| 24 | —CH=CH$_2$ | n$_D^{27}$ 1.6422 |
| 25 | —CH$_2$Cl | Melting point 96.2° C. |
| 26 | —CHClCH$_2$Cl | n$_D^{16}$ 1.6103 |
| 27 | —CH$_2$CN | n$_D^{18}$ 1.6167 |
| 28 | —CH$_2$CH$_2$OCH$_2$CH$_3$ | n$_D^{24}$ 1.6009 |
| 29 | —CH$_2$CSH$_3$ | n$_D^{13.5}$ 1.6412 |
| 30 | —CH$_2$CONH$_2$ | Viscous oily substance 3.64 (m, 2H), 4.20 (m, 3H), 5.27 (br, 2H) 6.96, 7.05, 7.52 (1H on hetero ring for each) |
| 31 | —CH$_2$CH$_2$COCH$_3$ | n$_D^{18}$ 1.6086 |
| 32 | —CH$_2$O$_2$CCH=CH$_2$ | n$_D^{18}$ 1.6082 |
| 33 | ⌬ | n$_D^{24}$ 1.6417 |
| 34 | Cl-⌬ | Melting point 119.4° C. (Z isomer) |

TABLE 1-continued (I)

[Structure: heterocyclic compound with NC, S, N, and R substituent as shown]

| Compound No. | R | Physical property, melting point, refractive index, NMR value (TMS/CDCl$_3$) |
|---|---|---|
| 35 | 2-Cl-phenyl | Melting point 141.5° C. (E isomer) |
| 36 | 3-Cl-phenyl | $n_D^{24}$ 1.6083 |
| 37 | 2-Br-phenyl | Viscous oily substance (Z isomer) 3.54–4.20 (m, 2H), 5.69 (DD, 1H), 7.00–7.75 (m, 7H) |
| 38 | 2-Br-phenyl | Viscous oily substance (E isomer) 3.45–4.10 (m, 2H), 5.76 (dd, 1H) 7.00–7.85 (m, 7H) |
| 39 | 4-Br-phenyl | Viscous oily substance (z isomer) 3.6–4.0 (m, 2H), 5.22 (dd, 1H) 6.9–7.81 (m, 7H) |
| 40 | 4-Br-phenyl | Melting point 148.8° C. (E isomer) |
| 41 | 2-F-phenyl | Viscous oily substance (Z isomer) |
| 42 | 2-F-phenyl | Melting point 119° C. (E isomer) |
| 43 | 4-F-phenyl | Viscous Oily substance 3.6–3.9 (m, 2H), 5.1–5.5 (m, 1H) 6.9–7.8 (m, 7H) |
| 44 | 2-CH$_3$-phenyl | $n_D^{18}$ 1.6313 (Z isomer) |
| 45 | 2-CH$_3$-phenyl | Melting point 123.3° C. (E isomer) |
| 46 | 4-CH$_3$-phenyl | $n_D^{24}$ 1.6360 |
| 47 | 2-i-C$_3$H$_7$-phenyl | $n_D^{16}$ 1.6196 |
| 48 | 2-CH$_3$O-phenyl | Viscous oily substance (Z isomer) |
| 49 | 2-CH$_3$O-phenyl | Viscous oily substance (E isomer) 3.71 (d, 2H), 3.82 (s, 3H), 5.68 (t, 1H) 6.87, 7.00, 6.72 (1H, for each, H on azole ring) 7.00–7.60 (m, 4H) |
| 50 | 4-OCH$_3$-phenyl | Viscous oily substance (Z isomer) 3.75 (d, 2H), 3.77 (s, 3H), 5.17 (t, 1H), 6.74–7.60 (m, 7H) |
| 51 | 4-OCH$_3$-phenyl | Viscous oily substance (E isomer) 3.67 (d, 2H), 3.80 (s, 3H), 5.24 (t, 1H), 6.70–7.65 (m, 7H) |
| 52 | 2,4-di-Cl-phenyl | Melting point 110.5° C. (Z isomer) |
| 53 | 2,4-di-Cl-phenyl | Melting point 100.4° C. (E isomer) |

TABLE 1-continued

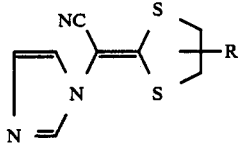

(I)

| Compound No. | R | Physical property, melting point, refractive index, NMR value (TMS/CDCl₃) |
|---|---|---|
| 54 | 2,3-dichlorophenyl | Viscous oily substance (Z isomer) |
| 55 | 2,3-dichlorophenyl | Viscous oily substance (E isomer) 3.42 (dd, 1H), 4.43 (t, 1H), 6.16 (dd, 1H), 7.18–7.40 (m, 3H), 6.98, 7.08, 7.56 (1H for each, H on azole ring) |
| 56 | 3,4-dichlorophenyl | Viscous oily substance 3.6–3.9 (m, 2H), 5.0–5.4 (m, 1H), 6.9–7.8 (m, 6H) |
| 57 | 3,4-methylenedioxyphenyl | Viscous oily substance 3.64, 3.72 (d, 2H for each), 5.11, 5.19 (t, 1H for each), 5.92, 5.95 (s, 2H for each), 6.60–6.95 (m, 3H), 7.00, 7.08, 7.53 (1H for each, H on azole ring) |
| 58 | 2,4,6-trimethylphenyl | Melting point 187.5° C. (Z isomer) |
| 59 | 2,4,6-trimethylphenyl | Melting point 214.0° C. (E isomer) |
| 60 | —CH₂—phenyl | Melting point 102.7° C. |
| 61 | —CH₂—(3,4-methylenedioxyphenyl) | $n_D^{17}$ 1.6258 |

TABLE 1-continued

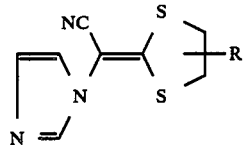

(I)

| Compound No. | R | Physical property, melting point, refractive index, NMR value (TMS/CDCl₃) |
|---|---|---|
| 62 | —CH₂O—phenyl | $n_D^{18}$ 1.6315 |
| 63 | —CH₂O—(4-chlorophenyl) | $n_D^{18}$ 1.6213 |
| 64 | 2-naphthyl | Melting point 135.0° C. |
| 65 | 2-pyridyl | Viscous oily substance 3.65–4.38 (m, 2H), 5.22–5.60 (m, 1H), 7.00–7.95 (m, 6H), 8.54–8.76 (m, 1H) |
| 66 | 2,3-dichlorophenyl | Viscous oily substance 3.75 (m, 2H), 5.20 (m, 1H), 6.80–7.80 (m, 7H) |
| 67 | 2-(difluoromethoxy)phenyl (F₂HCO) | $n_D^{18.5}$ 1.6063 |
| 68 | 2,4-difluorophenyl | Viscous oily substance (Z isomer) 3.83 (m, 2H), 5.46 (dd, 1H), 6.70–7.80 (m, 6H) |
| 69 | 2,4-difluorophenyl | Viscous oily substance (E isomer) 3.75 (m, 2H), 5.52 (dd, 1H), 6.60–7.80 (m, 6H) |
| 70 | 2,3-dichlorophenyl | $n_D^{17.5}$ 1.6358 (E isomer) |
| 71 | 2,3-dichlorophenyl | $n_D^{17.5}$ 1.6458 (Z isomer) |

TABLE 1-continued

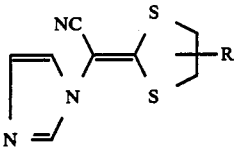

| Compound No. | R | Physical property, melting point, refractive index, NMR value (TMS/CDCl₃) |
|---|---|---|
| 72 | 4-F, 2-Cl phenyl | Viscous oily substance (Z isomer) 3.83 (m, 2H), 5.59 (dd, 1H), 6.75–7.70 (m, 6H) |
| 73 | 4-F, 2-Cl phenyl | m.p. 146–152° C. (E isomer) |
| 74 | 4-Cl, 2-F phenyl | Viscous oily substance (Z isomer) 3.38 (m, 2H), 5.42 (dd, 1H), 6.90–7.70 (m, 6H) |
| 75 | 4-Cl, 2-F phenyl | m.p. 114–117° C. (E isomer) |
| 76 | phenoxyphenyl | $n_D^{22.0}$ 1.6401 |
| 77 | phenoxyphenyl | $n_D^{22.0}$ 1.6262 |
| 78 | 2-methylpyridinyl | $n_D^{25.5}$ 1.6432 |
| 79 | 4-methylpyridinyl | $n_D^{25.5}$ 1.6332 |

Preferred compounds are these in which R represents a lower alkyl group, a lower alkyl group substituted by a lower alkoxyl or alkylthio group, or

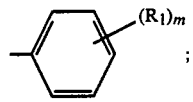

in which R₁ represents a halogen atom, especially chlorine or bromine atom, or a straight or branched chain lower alkyl group, especially methyl, and m represents an integer of 1 to 3.

Examples of this invention are shown below.

EXAMPLE 1

Synthesis of 2-(1-imidazolyl)-2-(4-isobutyl-1,3-dithiolan-2-ylidene)acetonitrile (Compound Nos. 8 and 9)

To a mixed solution of 0.55 g (0.005 mole) of 1-cyanomethylimidazole, 0.4 g (0.005 mole) of carbon disulfide and 10 ml of dimethyl sulfoxide was added 0.8 g (0.014 mole) of potassium hydroxide powder with stirring, and the reaction was carried out at room temperature for 1 hour. Then, 1.5 g (0.006 mole) of 1,2-dibromo-4-methylpentane was added dropwise with stirring, and the resulting solution was subjected to reaction for 2 hours. After completion of the reaction, 20 ml of water was added to the reaction solution, after which the resulting mixture was subjected to extraction with ethyl acetate, and the organic layer was washed with water and dried. The solvent was distilled off and the residue was purified by silica gel chromatography to obtain 0.45 g of the Z isomer and 0.3 g of the E isomer individually in the form of colorless crystals.

The Z isomer (Compound No. 8): melting point 73.3° C., yield 34%.

The E isomer (Compound No. 9): melting point 118.1° C., yield 23%.

EXAMPLE 2

Synthesis of 2-(1-imidazolyl)-2-(4-chloromethyl-1,3-dithiolan-2-ylidene)acetonitrile (Compound No. 25)

To a mixed solution of 0.55 g (0.005 mole) of 1-cyanomethylimidazole, 0.4 g (0.005 mole) of carbon disulfide and 10 ml of dimethyl sulfoxide was added 0.8 g (0.014 mole) of potassium hydroxide power with stirring, and the reaction was carried out at room temperature for 1 hour. Then, 1.4 g (0.006 mole) of 1,2-dibromo-3-chloropropane was added dropwise with stirring, and the resulting solution was subjected to reaction for 2 hours. After completion of the reaction, 20 ml of water was added to the reaction solution, after which the resulting mixture was subjected to extraction with ethyl acetate, and the organic layer was washed with water and dried. The solvent was distilled off and the residue was purified by silica gel chromatography and recrystallized from ethyl acetate-n-hexane to obtain 0.8 g of the desired compound in the form of colorless crystals: melting point 96.2° C., yield 62%.

EXAMPLE 3

Synthesis of 2-(1-imidazolyl)-2-(4-methylidene-1,3-dithiolan-2-ylidene)acetonitrile (Compound No. 23)

In 10 ml of tetrahydrofuran were dissolved 0.52 g (0.002 mole) of the 2-(1-imidazolyl)-2-(4-chloromethyl-1,3-dithiolan-2-ylidene)acetonitrile obtained in Example 2 and 0.31 g of 1,8-diazabicyclo-[5,4,0]-7-undecene, and the reaction was carried out with heating under reflux for 1 hour. After the reaction solution was allowed to cool, the deposited salt was separated by filtration and the filtrate was concentrated to obtain crude crystals, which were then recrystallized from ethyl acetate-n-hexane to obtain 0.35 g of the desired compound in the form of crystals: melting point 115.7° C., yield 79%.

EXAMPLE 4

Synthesis of 2-(1-imidazolyl)-2-[4-(2,4-dichlorophenyl)-1,3-dithiolan-2-ylidene]acetonitrile (Compound Nos. 52 and 53)

To a mixed solution of 0.55 g (0.005 mole) of 1-cyanomethylimidazole, 0.4 g (0.005 mole) of carbon disulfide and 10 ml of dimethyl sulfoxide was added 0.8 g (0.014 mole) of potassium hydroxide powder with stirring, and the reaction was carried out at room temperature for 1 hour. Then, 2.0 g (0.006 mole) of 2',4'-dichloro-1,2-dibromoethylbenzene was added dropwise with stirring, and the resulting solution was subjected to reaction for 2 hours. After completion of the reaction, 20 ml of water was added to the reaction solution, and the resulting mixture was subjected to extraction with ethyl acetate, and the organic layer was washed with water and dried. The solvent was distilled off and the residue was purified by silica gel chromatography to obtain 0.25 g of the Z isomer and 0.5 g of the E isomer individually in the form of a yellow viscous substance: yield (total yield of the Z and E isomers) 42%, melting points 110.5° C. (the Z isomer) and 100.4° C. (the E isomer).

EXAMPLE 5

Synthesis of 2-(1-imidazolyl)-2-[4-(2-isopropylphenyl)-1,3-dithiolan-2-ylidene]acetonitrile (Compound No. 47)

To mixed solution of 0.55 g (0.005 mole) of 1-cyanomethylimidazole, 0.4 (0.005 mole) of carbon disulfide and 10 ml of dimethylformamide was added 0.8 g (0.014 mole) of potassium hydroxide powder, and the reaction was carried out with stirring at room temperature for 1 hour. Then, 1.8 g (0.006 mole) of 2'-isopropyl-1,2-dibromoethylbenzene was added dropwise with stirring, and the resulting solution was subjected to reaction for another 2 hours. After completion of the reaction, 20 ml of water was added to the reaction solution, and the resulting mixture was subjected to extraction with ethyl acetate, and the organic layer was washed with water and dried. The solvent was distilled off and the residue was purified by silica gel chromatography to obtain the desired compound in the form of a light-yellow oily substance: $n_D^{16}$ 1.6196, yield 34%.

EXAMPLE 6

Synthesis of 2-(1-imidazolyl)-2-[4-(2-chlorophenyl)-1,3-dithiolan-2-ylidene]acetonitrile (Compound Nos. 34 and 35)

To a mixed solution of 2.2 g (0.02 mole) of 1-cyanomethylimidazole, 1.60 g (0.02 mole) of carbon disulfide and 10 ml of dimethyl sulfoxide was added 3.0 g (0.05 mole) of potassium hydroxide powder, and the reaction was carried out with stirring at room temperature for 1 hour. Then, 4.2 g (0.02 mole) of 2'-chloro-(1,2-dichloroethyl)benzene was added dropwise with stirring, and the resulting solution was subjected to reaction for another 2 hours. After completion of the reaction, 20 ml of water was added to the reaction solution, after which the resulting mixture was subjected to extraction with ethyl acetate, and the organic layer was washed with water and dried. The solvent was distilled off and the residue was purified by silica gel chromatography to obtain 2.0 g of the Z isomer and 2.4 g of the E isomer individually in the form of light-yellow crystals.

The Z isomer: melting point 119.4° C., yield 31%.
The E isomer: melting point 141.5° C., yield 38%.

EXAMPLE 7

Synthesis of 2-(1-imidazolyl)-2-[4-(2-chlorophenyl)-1,3-dithiolan-2-ylidene]acetonitrile (Compound Nos. 34 and 35)

To a mixed solution of 2.2 g (0.02 mole) of 1-cyanomethylimidazole, 1.60 g (0.02 mole) of carbon disulfide and 10 ml of dimethyl sulfoxide was added 3.0 g (0.05 mole) of potassium hydroxide powder, and the reaction was carried out with stirring at room temperature for 1 hour. Then, 6.0 g (0.02 mole) of 2'-chloro-(1,2-dibromoethyl)benzene was added dropwise with stirring, and the resulting solution was subjected to reaction for another 2 hours. After completion of the reaction, 20 ml of water was added to the reaction solution, after which the resulting mixture was subjected to extraction with ethyl acetate, and the organic layer was washed with water and dried. The solvent was distilled off and the residue was purified by silia gel chromatography to obtain 0.3 g of the Z isomer and 1.3 g of the E isomer individually in the form of light-yellow crystals.

The Z isomer: melting point 119.4° C., yield 5%.
The E isomer: melting point 141.5° C., yield 20%.

EXAMPLE 8

Synthesis of 2-(1-imidazolyl)-2-[4-(2-chlorophenyl)-1,3-dithiolan-2-ylidene]acetonitrile (Compound Nos. 34 and 35)

To a mixed solution of 2.2 g (0.02 mole) of 1-cyanomethylimidazole, 1.60 g (0.02 mole) of carbon disulfide and 10 ml of dimethyl sulfoxide was added 3.0 g (0.05 mole) of potassium hydroxide powder, and the reaction was carried out with stirring at room temperature for 1 hour. Then, 6.6 g (0.02 mole) of 2'-chloro-(1,2-dimesyloxyethyl)benzene was added dropwise with stirring, and the resulting solution was subjected to reaction for another 2 hours. After completion of the reaction, 20 ml of water was added to the reaction solution, after which the resulting mixture was subjected to extraction with ethyl acetate, and the organic layer was washed with water and dried. The solvent was distilled off and the residue was purified by silica gel chromatography to obtain 1.3 g of the Z isomer and 1.8 g of the E isomer individually in the form of light-yellow crystals.

The Z isomer: melting point 119.4° C., yield 20%.
The E isomer: melting point 141.5° C., yield 28%.

The compounds of this invention are antimycotic agents useful for preventing fungous infection of human beings and animals. For example, these compounds can be used for curing mycoses such as local mycotic infection, mucosal mycotic infection, systemic mycotic infection and the like which are caused by Dermatophytes such as Microsporum, Epidermophyton, Trichophyton and the like and Candida.

The compounds of this invention can be mixed with conventional chemotherapeutically acceptable diluents or carriers and if desired, other excipients, and can be used in pharmaceutical forms such as solutions, creams, suppositories, ointments, tablets, etc.

When used as antimycotic agents, the compounds of this invention can be used as local liniments in pharmaceutical forms such as creams, ointments, solution, etc. When they are used in the form of an endermic solution, their practical concentration is considered to be suitably 0.1% or more.

The present drugs may be used, of course, in an admixture with other antibacterial agents such as amphotericin B, nystatin, trichomycin, variotin, clotrimazole and the like.

Further, the compounds of this invention are useful as agricultural and horticultural fungicides. For example, they are very effective against various phytopathogenic diseases, e.g., rice blast (*Piricularia oryzae*); powdery mildew of barley and wheat (*Erysiphe graminis*), and other powdery mildews of various host plants such as that of cucumber (*Sphaerotheca fulginea*), that of apple (*Podosphaera leucotricha*) and that of grape (*Uncinula necator*); rust of wheat (*Puccinia vecondita*); Crown rust of oats (*Puccinia coronate*) and rust of other host plants: late blight of tomato (*phytophthora capsici*) and phytophthora rot of other host plants; etc.

When the compound of this invention is used as active ingredient in an agricultural and a horticultural fungicide, the fungicide is prepared into a formulation suitable for use in a conventional manner as an agricultural chemical. For example, the fungicide is prepared in the form of dust, granules, fine granules, wettable powder, emulsifiable concentrate, oily solution, aerosol, floating dust, fumigants, preparations suitable for vaporizing the active ingredient by heat or other physical means, tablets or the like by mixing the compound of the invention with adjuvants, and is applied to stalks and leaves of vegetables, flowering plants, crops for industrial use, fruit trees, other trees and the like as it is or after diluted to a suitable volume with water. Although in this invention the dosage of the active ingredient varies depending on the kind of the compound, plant to be treated, the way of using, and the like, it can be selected in the range of 5 to 500 g per 10 ares.

When applied, the compound of this invention can also be used in admixture with or in combination with other agricultural chemicals, fertilizers, plant nutrients and the like which can be used similarly to the compound.

For example, when a phytopathogenic disease is controlled by using an agricultural and horticultural fungicide comprising the compound of this invention as active ingredient, the fungicide can be made into a multiple-purpose preventing and curing agent by mixing therewith an agent for preventing and curing other diseases and/or vermin insects which break out simultaneously with aforesaid disease.

Next, some test examples and formulation examples are given below in order to demonstrate the usefulness of the compounds of this invention, but this invention is not intended to be limited thereto.

TEST EXAMPLE 1

Test for antifungal activity against *Trichophyton mentagrophytes*

In 1 liter of water were dissolved 10 g of peptone and 4.0 g of glucose and the resulting solution was adjusted to pH 6.0, after which a drug containing 50 ppb (1% DMSO solution) of each active ingredient was added. Into a 3.5 φ cm Petri dish was poured 30 ml of the thus obtained Sabouraud medium to prepare an agar plate. Then, the inoculum of the fungus precultured was poured onto the plate in an amount of 0.1 ml per Petri dish. Thus prepared plates were incubated at 28° C. for 4–6 days. The test was carried out in duplication for each compound and the results per dish evaluated macroscopically are shown in Table 2. Evaluation criterion
+ Multiplication of cells was completely inhibited.
± Multiplication of cells was inhibited.
+ + White colonies were formed.
+ + + The diameter of white colonied increased.

TABLE 2

| Compound No. | Degree of growth | |
|---|---|---|
| 4 | ± | + |
| 28 | ± | + |
| 33 | ± | ± |
| 35 | ± | + |
| 36 | ± | ± |
| 37 | ± | ± |
| 38 | + | + |
| 39 | ± | ± |
| 40 | ± | ± |
| 41 | + | + + |
| 42 | + | ± |
| 43 | ± | ± |
| 46 | ± | ± |
| 52 | ± | ± |
| 53 | ± | ± |
| 59 | ± | ± |
| 64 | + | + |
| 65 | + | + |
| Control (no compound added) | | |

TEST EXAMPLE 2

Curing effect test against trichophytosis which was artificially infected in guinea pigs Hartley strain white male guinea pigs (400 to 600 g) were used as test animals. The hair in three spots on the back of each guinea pig was sheared and then removed in a circle having a diameter of about 3 cm by use of depilatory cream, after which the skin in the depilated spots was lightly rubbed with sandpaper. Thus treated spots were inoculated with 0.1 ml ($10^6$ spores/spot) of culture of *Trichophyton mentagrophytes* IFO-5466 strain grown on Sabouraud glucose agar media. Each test drug prepared by using polyethylene glycol 300 as base was applied to the inoculation spots once daily for 11 consecutive days in an amount of 0.2 ml per inoculation spot, starting 72 hours after the inoculation. The evaluation was conducted by macroscopical judgement and reverse culture test.

(a) Macroscopical judgement:

After the inoculation, the alleviation and development of symptoms in the above-mentioned spots were observed every day for 15 days. The results are shown in Table 3.
0: No symptom was observed.
1: A few small erythemas were observed.
2: Erythemas were insularly scattered or fused into one, and rubefaction was observed around them.
3: Scales were observed, and then formation of thick lesion was observed.
4: Lesion reached to an extreme stage with bleeding.
The results obtained are shown in Table 3.

(b) Reverse culture test

Each guinea pig was sacrified 15 days after the inoculation, after which the skin in the whole inoculation spots was cut off and the skin cut-off was further cut into small pieces (about 5 mm square). The pieces thus prepared were placed on Sabouraud glucose agar medium containing 20 i.u./ml of penicillin G and 40 μg/ml of streptomycin, and then cultured at 27° C. for 2 weeks. The evaulation was carried out by investigating the colonies. The results obtained are shown in Table 4.

TABLE 3

(Macroscopical judgement)

| Drug tested (Concentration) | Days | | | | | | | | | | | |
|---|---|---|---|---|---|---|---|---|---|---|---|---|
| | 4 | 5 | 6 | 7 | 8 | 9 | 10 | 11 | 12 | 13 | 14 | 15 |
| Compound 53 | | | | | | | | | | | | |
| (1%) | 0.5 | 1 | 1 | 1 | 1 | 1 | 1 | 1.5 | 1.5 | 1.5 | 2.5 | 2 |
| (0.1%) | 1 | 2 | 2 | 2 | 2.5 | 3 | 3 | 3.5 | 3.5 | 3.5 | 3.5 | 3.5 |
| Compound 35 | | | | | | | | | | | | |
| (1%) | 1 | 1 | 1 | 1 | 1 | 1 | 1.5 | 1.5 | 1.5 | 1.5 | 3 | 3 |
| (0.1%) | 0.5 | 1 | 1.5 | 1.5 | 2 | 2.5 | 3 | 3.5 | 3.5 | 3.5 | 3.5 | 4 |
| Compound 38 | | | | | | | | | | | | |
| (1%) | 1 | 1.5 | 1.5 | 1 | 1 | 1 | 1.5 | 2 | 2 | 2 | 2 | 2 |
| (0.1%) | 0.5 | 2 | 2 | 2 | 2.5 | 2.5 | 3 | 3 | 3.5 | 3.5 | 3.5 | 4 |
| Tolnaftate | | | | | | | | | | | | |
| (1%) | 1 | 1 | 1 | 1.5 | 1 | 1 | 1.5 | 2 | 2.5 | 2.5 | 3.5 | 3.5 |
| (0.1%) | 0 | 1.5 | 1.5 | 2 | 2.5 | 3 | 3 | 3 | 3 | 3 | 3 | 3 |
| Control (No compound treated) | 1 | 2 | 2 | 2 | 3 | 3.5 | 3.5 | 3.5 | 3.5 | 4 | 4 | 4 |

TABLE 4

(Results of reverse culture test)

| Drug Tested | Concentration | |
|---|---|---|
| | 1% | 0.1% |
| Compound 53 | 0/20 | 7/20 |
| Compound 35 | 0/20 | 6/20 |
| Compound 38 | 0/20 | 6/20 |
| Tolnaftate | 0/20 | 16/20 |
| Control (No compound treated) | 20/20 | |

TEST EXAMPLE 3

Controlling Effects on Powdery Mildew of Barley

Young barley plants (variety: Kanto No. 6, 2-leaf stage) cultivated in the porcelain pots (12 cm in diameter) were inoculated by conidia of *Erysiphe graminis graminis F.Sp. hordei*, the causal fungus of powdery mildew. The day after inoculation, the plants were treated on the turn table by spraying solutions (200 ppm) of the present compounds by spray gun. The treated plants were kept at 25° C. for 6 days in a greenhouse and the development of lesions was assessed. The controlling effects of the compounds were calculated in comparison with the untreated plots.

The criteria for the controlling effects are:
4; 100–95% control
3; 94–80% control
2; 79–60% control
1; 59–0% control
The results are shown in Table 5.

TABLE 5

| Compound No. | Concentration (ppm) | Controlling effects | Compound No. | Concentration (ppm) | Controlling effects |
|---|---|---|---|---|---|
| 1 | 200 | 3 | 38 | 200 | 4 |
| 3 | " | 4 | 42 | " | 4 |

TABLE 5-continued

| Compound No. | Concentration (ppm) | Controlling effects | Compound No. | Concentration (ppm) | Controlling effects |
|---|---|---|---|---|---|
| 5 | " | 4 | 43 | " | 4 |
| 8 | " | 4 | 45 | " | 4 |
| 9 | " | 4 | 46 | " | 4 |
| 12 | " | 3 | 47 | " | 4 |
| 15 | " | 4 | 48 | " | 4 |
| 17 | " | 4 | 50 | " | 4 |
| 20 | " | 4 | 53 | " | 4 |
| 21 | " | 4 | 54 | " | 4 |
| 22 | " | 4 | 56 | " | 4 |
| 24 | " | 4 | 57 | " | 4 |
| 25 | " | 4 | 58 | " | 4 |
| 26 | " | 4 | 61 | " | 4 |
| 27 | " | 2 | 62 | " | 4 |
| 28 | " | 4 | 64 | " | 4 |
| 29 | " | 4 | 65 | " | 4 |
| 30 | " | 2 | 67 | " | 4 |
| 32 | " | 2 | 72 | " | 4 |
| 33 | " | 4 | 75 | " | 4 |
| 34 | " | 4 | 76 | " | 4 |
| 35 | " | 4 | 77 | " | 4 |
| 36 | " | 4 | 78 | " | 4 |
| 37 | " | 4 | 79 | " | 4 |

TEST EXAMPLE 4

Controlling Effects on Seen-borne Fusarium

Cucumber seeds infested with *Fusarium oxysporum f.sp. cucumerinum* were soaked in solutions (200 ppm) of the present compounds for 20 hr. The treated seeds were then placed on the selective medium for Fusarium spp. (Komada medium). After a week-incubation at 25° C., the mycelial growth around the treated seeds was assessed and the controlling effects were calculated in comparison with untreated plots. The criteria for controlling effects are as same as in Test Example 3.

The results are shown in Table 6.

TABLE 6

| Compound No. | Concentration (ppm) | Controlling effects | Compound No. | Concentration (ppm) | Controlling effects |
|---|---|---|---|---|---|
| 3 | 200 | 4 | 52 | 200 | 4 |
| 4 | " | 4 | 53 | " | 4 |
| 6 | " | 4 | 54 | " | 4 |
| 7 | " | 4 | 55 | " | 4 |
| 10 | " | 4 | 56 | " | 4 |
| 11 | " | 4 | 57 | " | 4 |
| 13 | " | 4 | 58 | " | 3 |
| 16 | " | 4 | 60 | " | 4 |
| 18 | " | 4 | 61 | " | 4 |
| 20 | " | 4 | 63 | " | 4 |
| 21 | " | 4 | 64 | " | 4 |
| 24 | " | 3 | 65 | " | 4 |
| 26 | " | 2 | 66 | " | 4 |
| 29 | " | 4 | 67 | " | 2 |
| 33 | " | 4 | 68 | " | 4 |
| 35 | " | 4 | 69 | " | 4 |
| 37 | " | 4 | 70 | " | 4 |
| 39 | " | 4 | 71 | " | 4 |
| 40 | " | 4 | 73 | " | 4 |
| 44 | " | 4 | 75 | " | 4 |
| 47 | " | 4 | 76 | " | 4 |
| 49 | " | 4 | 77 | " | 4 |
| 50 | " | 4 | 78 | " | 4 |
| 51 | " | 4 | 79 | " | 4 |

The recipes shown below as Formulation Examples 1 to 3 are for medical purposes. For these purposes, the various adjuvants and constituents to be used should be of pharmaceutically acceptable grade. In Formulation Examples 1 to 3, all parts are by weight.

FORMULATION EXAMPLE 1

| Compound 35 | 1 part |
|---|---|
| Polyethylene glycol 300 | 95 parts |

These ingredients are mixed to prepare an endermic solution.

FORMULATION EXAMPLE 2

| Compound 53 | 2 parts |
|---|---|
| Polyethylene glycol 400 | 40 parts |
| Polyethylene glycol 1500 | 58 parts |

These ingredients are mixed with heating to obtain a solution, which is then colled to prepare an ointment.

FORMULATION EXAMPLE 3

| Copmpound 38 | 2 parts |
|---|---|
| 1,2-Propanediol | 5 parts |
| Glycerol stearate | 5 parts |
| Spermaceti | 5 parts |
| Isopropyl myristate | 10 parts |
| Polysorbate 60 | 4 parts |

A mixture of them is heated and then cooled, after which 69 parts of water is added with stirring to prepare cream.

In addition to the pharmaceutical formulations described above, preparation in pharmaceutically usable forms such as injections, tablets and the like is possible.

The recipes shown in Formulation Examples 4 to 7 are for agricultural chemicals. In these examples, all parts are by weight as in Formulation Examples 1 to 3.

FORMULATION EXAMPLE 4

Wettable Powder

| Compound 12 | 50 parts |
|---|---|
| Mixture of diatomaceous earth and clay | 45 parts |
| Polyoxyethylene nonylphenyl ether | 5 parts |

These ingredients are homogeneously mixed and then pulverized to prepare a wettable powder.

FORMULATION EXAMPLE 5

Emulsifiable Concentrate

| Compound 23 | 20 parts |
|---|---|
| Tetrahydrofuran | 20 parts |
| Xylene | 45 parts |
| Mixture of polyoxyethylene nonylphenyl ether and alkyl benzenesulfonate | 15 parts |

These ingredients are homogeneously mixed to prepare an emulsifiable concentrate.

FORMULATION EXAMPLE 6

Dust

| Compound 29 | 4 parts |
|---|---|
| Mixture of diatomaceous earth, clay and talc | 95 parts |
| Calcium stearate | 1 part |

These ingredients are homogeneously mixed and then pulverized to prepare a dust.

FORMULATION EXAMPLE 7

Granules

| Compound 46 | 3 parts |
|---|---|
| Mixture of bentonite and clay | 92 parts |
| Calcium lignin sulfonate | 5 parts |

These ingredients are homogeneously mixed and then pulverized, after which an adequate amount of water is added, and the resulting mixture is sufficiently kneaded and then granulated to prepare granules.

What is claimed is:

1. A fungicidal composition for controlling phytopathogenic fungi comprising a fungicidally effective amount of a ketene S,S-acetal derivative represented by the general formula (I):

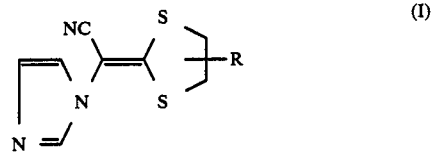

wherein R represents a hydrogen atom; an alkyl group having 1 to 8 carbon atoms; a cycloalkyl group having 3 to 6 carbon atoms; a methylene group; a lower alkenyl group; a lower alkyl group substituted by a halogen atom; a cyano group, a lower alkoxyl group, a lower alkylthio group, a carbamoyl group, a lower alkanoyl group, or an alkenoyloxy group; a phenyl group represented by

(in which $R_1$ represents a hydrogen atom, a halogen atom, a straight or branched chain lower alkyl group, a lower alkoxyl group which may be substituted by one or more halogen atoms, a phenoxy group or a methylenedioxy group, and m represents an integer of 1 to 3); a benzyl group, a methylenedioxybenzyl group; a phenoyalkyl group; a phenoxyalkyl group substituted by a halogen atom; a naphthyl group; a pyridyl group or a pyridyl group substituted by a lower alkyl group, and a suitable carrier.

2. A fungicidal composition according to claim 1, wherein said composition is used for seed treatment.

3. A fungicidal composition according to claim 1 or 2, wherein the ketene S,S-acetal derivative is 2-(1-imidazolyl)-2-[4-(2-chlorophenyl)-1,3-dithiolan-2-ylidene]acetonitrile (E isomer).

4. A fungicidal composition according to claim 1 or 2 wherein the ketene S,S-acetal derivative is 2-(1-imidazolyl)-2-[4-(2,4-dichlorophenyl)-1,3-dithiolan-2-ylidene]acetonitrile (E-isomer).

5. A fungicidal composition according to claim 1 or 2, wherein the ketene S,S-acetal derivative is 2-(1-imidazolyl)-2-[4-(2-bromophenyl)-1,3-dithiolan-2-ylidene]acetonitrile (E-isomer).

6. A method for controlling fungal diseases of agricultural and horticultural crop which comprises applying to said crops a fungicidally effective amount of a ketene S,S-acetal derivative represented by the general formula (1)

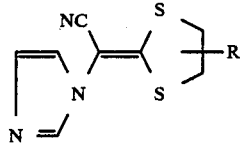

(I)

wherein R represents a hydrogen atom; an alkyl group having 1 to 8 carbon atoms; a cycloalkyl group having 3 to 6 carbon atoms; a methylen group; a lower alkenyl group; a lower alkyl group substituted by a halogen atom; a cyano group, a lower alkyloxyl group, a lower alkylthio group, a carbamoyl group, a lower alkanoyl group, or analkenoyloxy group; a phenyl group represented by

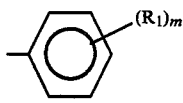

(in which $R_1$ represents a hydrogen atom, a halogen atom, a straight or branched chain lower alkyl group, a lower alkoxy group which may be substituted by one or more halogen atoms, a phenoxy group or a methylenedioxy group, and m represents an integer of 1 to 3); a benzyl group, a methylenedioxybenzyl group; a phenoxyalkyl group; a phenoxyalkyl group substituted by a halogen atom; a naphthyl group; a pyridyl group or a pyridyl group substituted by a lower alkyl group.

7. The method for controlling fungal diseases of agricultural and horticultural crops according to claim 6, wherein said ketene is applied to seed treatment.

8. The method for controlling fungal diseases of agricultural and horticultural crops according to claim 6 or 7, wherein the ketene S,S-acetal derivative is 2-(1-imidazolyl)-2-[4-(2-chlorophenyl)-1,3-dithiolan-2-ylidene]acetonitrile (E isomer).

9. The method for controlling fungal diseases of agricultural and horticultural crop according to claim 6 or 7, wherein the ketene S,S-acetal derivative is 2-(1-imidazolyl)-2-[4-(2,4-dichlorophenyl)-1,3-dithiolan-2-ylidene]acetonitrile (E isomer).

10. The method for controlling fungal diseases of agricultural and horticultural crop according to claim 6 or 7, where in the ketene S,S-acetal is 2-(1-imidazolyl)-2[4-(2-bromophenyl)-1,3-dithiolan-2-ylidene]acetonitrile (E isomer).

11. A pharmaceutical composition for controlling mycosis, comprising a pharmaceutically effective amount of a ketene S,S-acetal derivative represented by the general formula (1)

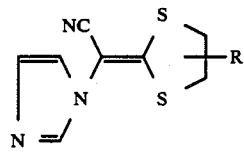

(I)

wherein R represents a hydrogen atom; an alkyl group having 1 to 8 carbon atoms; a cycloalkyl group having 3 to 6 carbon atoms; a methylene group; a lower alkenyl group; a lower alkyl group substituted by a halogen atom; a cyano group, a lower alkoxyl group, a lower alkylthio group, a carbamoyl group, a lower alkanoyl group, or an alkenoyloxy group; a phenyl group represented by

(in which $R_1$ represents a hydrogen atom, a halogen atom, a straight or branched chain lower alkyl group, a lower alkoxyl group which may be substituted by one or more halogen atoms, a phenoxy group or a methylenedioxy group, and m represents an integer of 1 to 3); a benzyl group, methylenedioxybenzyl group; a phenoxyalkyl group; a phenoxyalkyl group substituted by a halogen atom; a naphthyl group; a pyridyl group or a pyridyl group substituted by a lower alkyl group, and a pharmaceutically acceptable carrier.

12. The pharmaceutical composition according to claim 11, wherein the active ingredient is formulated with a pharmaceutically acceptable diluent.

13. The pharmaceutical composition according to claim 11, wherein the composition is any form of solution, creams, suppositories, ointments, tablets.

14. The pharmaceutical composition according to claim 11, wherein the ketene S,S-acetal derivative is 2-(1-imidazolyl)-2-[4-(2,4-dichlorophenyl)-1,3-dithiolan-2-ylidene]acetonitrile (E isomer).

15. The pharmaceutical composition according to claim 11, wherein the ketene S,S-acetal derivative is 2-(1-imidazolyl)-2-[4-(2-chlorophenyl)-1,3-dithiolan-2-ylidene]acetonitrile (E isomer).

16. The pharmaceutical composition according to claim 11, wherein the ketene S,S-acetal derivative is 2-(1-imidazolyl)-2-[4-(2-bromophenyl)-1,3-dithiolan-2-ylidene]acetonitrile (E isomer).

* * * * *